United States Patent
Merianos

(10) Patent No.: US 6,340,707 B1
(45) Date of Patent: Jan. 22, 2002

(54) HIGH PURITY, CLEAR, LIGHT STABLE, FORMALDEHYDE-FREE PRESERVATIVE COMPOSITIONS CONTAINING A COMPOUND FORMED BY THE REACTION OF EXCESS GLYCINE AND FORMALDEHYDE AT LOW TEMPERATURES

(75) Inventor: John J. Merianos, Middletown, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/572,517

(22) Filed: May 17, 2000

(51) Int. Cl.$^7$ ............................................. A01N 37/02
(52) U.S. Cl. ...................................... 514/578; 562/575
(58) Field of Search ........................... 562/567; 514/578

(56) References Cited

U.S. PATENT DOCUMENTS 4,337,269 A * 6/1982 Berke et al. ................ 424/289

OTHER PUBLICATIONS

Krause, Hugo. Chemical Abstracts, vol. 14 (1920) pp. 56–57.*
Rodd, Chemistry of Carbon Compounds, vol. ID (1965) p. 167.*
Baur, Emil. Chemical Abstracts, vol. 34 (1940) p. 3971.*

* cited by examiner

Primary Examiner—Gary Geist
Assistant Examiner—Zachary C. Tucker
(74) Attorney, Agent, or Firm—Walter Katz; Wiliam J. Davis; Marilyn J. Maue

(57) ABSTRACT

A high purity, water-white, clear, light stable, non-toxic, formaldehyde-free composition for inhibiting growth in a substance requiring microbial inhibition comprising about 40–60% by weight of an aqueous solution of hydroxymethylaminoacetate in the form of its alkali metal salt which is formed by the reaction of a salt of glycine, with formaldehyde, in an aqueous medium, at a pH of about 10.5–12.5, characterized by carrying out the reaction at a molar ratio of glycine to formaldehyde sufficient to maintain a molar excess of glycine in the medium and to leave a predetermined amount of residual glycine present in the composition at the conclusion of the reaction, and to preclude the presence of any detectable free formaldehyde as methylene diol in said composition.

6 Claims, No Drawings

HIGH PURITY, CLEAR, LIGHT STABLE, FORMALDEHYDE-FREE PRESERVATIVE COMPOSITIONS CONTAINING A COMPOUND FORMED BY THE REACTION OF EXCESS GLYCINE AND FORMALDEHYDE AT LOW TEMPERATURES

BACKGROUND OF THE INVENTION

1. Field of the Invention

This invention relates to preservative compositions, and, more particularly, to high purity, clear, light stable, formaldehyde-free preservative compositions containing a compound formed by the reaction of excess glycine and formaldehyde at low temperatures.

2. Description of the Prior Art

P. Berke et al, in U.S. Pat. No. 4,337,269, described a biocidal composition containing the crystalline product obtained from the reaction of glycine and formaldehyde, at a 1:1 molar ratio of reactants. Under these reaction conditions, the product obtained included considerable amounts of free formaldehyde.

Accordingly, it is an object of this invention to provide a high purity, clear, light stable, formaldehyde-free biocidal composition of the reaction product of glycine and formaldehyde, with predetermined amounts of residual glycine therein and substantially no unwanted by-products of the reaction.

These and other objects and features of the invention will be made apparent from the following more detailed description hereinafter.

SUMMARY OF THE INVENTION

What is described herein is a high purity, clear, light stable, formaldehyde-free, non-toxic composition for inhibiting growth in a substance requiring microbial inhibition comprising about 40–60% by weight of an aqueous solution of hydroxymethyl aminoacetate in the form of its alkali metal salt which is formed by the reaction of excess glycine, a lower alkyl substituted glycinate, or salts thereof, with formaldehyde, in an aqueous medium, at a pH of about 10.5–12.5, characterized by carrying out the reaction at a molar ratio of glycine to formaldehyde necessary to maintain a molar excess of glycine in the medium and to leave a predetermined amount of residual glycine present in the composition at the conclusion of the reaction, and sufficient to preclude the presence of any detectable free formaldehyde as methylene diol in the resultant composition.

In suitable embodiments of the invention, the reaction between excess glycine and formaldehyde is carried out with a molar excess of glycine of 0.5 to 10% over a 1:1 molar ratio of glycine to formaldehyde; so that no free or residual formaldehyde as methylene diol can remain in the composition at the conclusion of the reaction. The residual excess glycine level in the composition is 750–35,000 ppm, preferably 1000–3000 ppm.

Preferably, the reaction is carried out at a temperature of <40° C., most preferably 10–25° C., whereat no unwanted by-products can form during the reaction.

DETAILED DESCRIPTION OF THE INVENTION

The overall chemistry of the reaction herein is given in Equation (A) below:

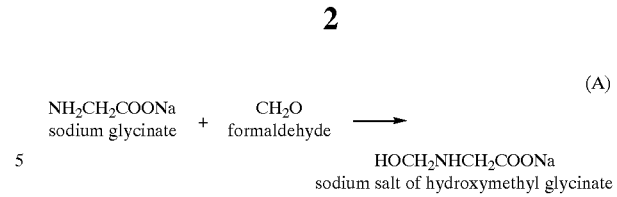

However, the reaction product can also undergo a dehydration reaction (B) to produce a Schiff base:

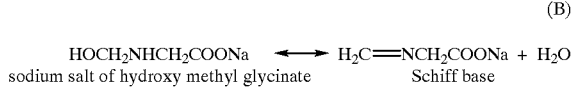

The Schiff base is a reactive species which can undergo various side reaction which produce unwanted by-products, such as cyclization reactions to form the corresponding lactones, as well as hexahydro-triazines, and polymeric products thereof. These side reactions are minimized herein because the main reaction is carried out at a low temperature, i.e. below 40° C. and preferably at about 10–25° C. At such low temperatures, formation of the Schiff base in reaction (B) is minimized. Thereby, the resultant reaction composition contains only a minimum amount of undesirable reaction by-products.

The invention will now be described with reference to the following examples.

INVENTION EXAMPLE 1

Glycine (82.5 g, 1.1 mole) was charged into a reactor and 40% aqueous sodium hydroxide (110 g, 1.1 mole) was added slowly with cooling below 15° C. Then a 37 wt% formaldehyde aqueous solution (81.0 g, 1.0 mole) was added slowly with cooling to keep the temperature below 40° C., optimally at 10–25° C. The pH of the resultant solution was 12.5 and it was adjusted to 11.5 with phosphoric acid. The final composition was a high purity, water-white, clear, light stable solution containing about 50% by wt. of hydroxymethyl glycinate sodium and no free formaldehyde, i.e. below the detectable limit of analytical equipment (<90 ppm). Substantially no reaction by-products were evident in the composition. The product was an effective biocide and without skin irritation in use in personal care formulations.

INVENTION EXAMPLES 2–5

The procedure of Example 1 was followed using excess glycine in predetermined amounts over a 1:1 molar ratio glycine to formaldehyde, with similar results. Examples 1–5 are summarized in the Table below:

TABLE

| Example No. Reactants ↓ | 1 Wt. (g) | 10% Excess Glycine Mole | 2 Wt. (g) | 5% Excess Glycine Mole | 3 Wt. (g) | 2% Excess Glycine Mole | 4 Wt. (g) | 1% Excess Glycine Mole | 5 Wt. (g) | 0.5 Excess Glycine Mole |
|---|---|---|---|---|---|---|---|---|---|---|
| Glycine (98%) | 82.5 | 1.1 | 78.75 | 1.05 | 76.5 | 1.02 | 75.75 | 1.01 | 75.37 | 1.005 |
| Sodium Hydroxide (40%) | 110.0 | 1.1 | 105.0 | 1.05 | 102.0 | 1.02 | 101.0 | 1.01 | 100.5 | 1.005 |
| Formaldehyde (37%) | 81.0 | 1.0 | 81.0 | 1.0 | 81.0 | 1.0 | 81.0 | 1.0 | 81.0 | 1.0 |

Invention Examples 1–5 above produced preservative compositions having no detectable residual methylene diol therein. Residual sodium glycinate was present in the compositions its amount increasing with the wt. % excess glycine used in the reactant mixture. Suitabley, in Example 1,750 ppm of residual glycinate remained, and up to 34,000 ppm was present (Example 5). The Examples 4 and 5, with 1 and 2 wt. % excess glycine reactant provided residual glycine amounts of about 2000 and 2500 ppm, respectively in the composition. Substantially no reaction by-products were evident in any of the examples.

COMPARATIVE EXAMPLE (Berke. P. Ex. 1)

A solution of 75 g (1.00 mole) of glycine in 100 9 (1.00 mole) of 40 wt. % aqueous sodium hydroxide was treated with 82 9 (1.00 mole) of 37 wt. % formaldehyde, a 1:1 molar ratio of glycine at 48° C. The final solution pH was 11.4. The resultant solution contained 281 ppm of residual methylene diol (i.e. free formaldehyde), a small amount of residual glycine, and some reaction by-products.

While the invention has been described with particular reference to certain embodiments thereof, it will be understood that changes and modifications may be made which are within the skill of the art. Accordingly, it is intended to be bound only by the following claims, in which:

What is claimed is:

1. A high purity, water-white, clear, light stable, non-toxic, formaldehyde-free composition for inhibiting growth in a substance requiring microbial inhibition comprising about 40–60% by weight of an aqueous solution of hydroxymethylaminoacetate in the form of its alkali metal salt which is formed by the reaction of a salt of glycine, with formaldehyde, in an aqueous medium, at a pH of about 10.5–12.5, characterized by carrying out the reaction at a temperature of about 15–25° C. and at a molar ratio of glycine to formaldehyde sufficient to maintain a molar excess of glycine of 0.5 to 10% in the medium and to leave a predetermined amount of residual glycine present in the composition at the conclusion of the reaction, and to preclude the presence of any detectable free formaldehyde as methylene diol in said composition as a result of unreacted formaldehyde.

2. A composition according to claim 1 wherein said molar excess is 1 to 2%.

3. A composition according to claim 1 which is about 48–52 wt.% aqueous solution of hydroxymethylaminoacetate.

4. A composition according to claim 1 wherein said residual glycine level is 750–35,000 ppm.

5. A composition according to claim 4 wherein said residual glycine level is about 1000–3000 ppm.

6. A product including the composition of claim 1.

* * * * *